United States Patent [19]

Lynn et al.

[11] Patent Number: 5,137,524
[45] Date of Patent: Aug. 11, 1992

[54] UNIVERSAL INTRAVENOUS CONNECTOR WITH DUAL CATCHES

[75] Inventors: Lawrence A. Lynn, 1275 Olentangy River Rd., Suite 202, Columbus, Ohio 43212; Mark E. Larkin, Lindenhurst, Ill.

[73] Assignee: Lawrence A. Lynn, Columbus, Ohio

[21] Appl. No.: 509,638

[22] Filed: Apr. 17, 1990

Related U.S. Application Data

[63] Continuation-in-part of Ser. No. 264,533, Oct. 31, 1988, abandoned, which is a continuation-in-part of Ser. No. 240,539, Sep. 6, 1988, Pat. No. 4,946,445.

[51] Int. Cl.$^5$ .............................................. A61M 25/00
[52] U.S. Cl. ..................................... 604/283; 604/414; 604/905
[58] Field of Search ................. 604/280, 283, 86, 905, 604/411–414, 198, 29, 87–88, 244

[56] References Cited

U.S. PATENT DOCUMENTS

| | | | |
|---|---|---|---|
| 4,405,163 | 9/1983 | Voges et al. | 604/283 |
| 4,675,020 | 6/1987 | McPhee | 604/411 |
| 4,759,756 | 7/1988 | Forman et al. | 604/88 X |
| 4,768,568 | 9/1988 | Fournier et al. | 604/905 X |
| 4,820,288 | 4/1989 | Isono | 604/283 |
| 4,895,570 | 1/1990 | Larkin | 604/411 |
| 4,963,133 | 10/1990 | Whipple | 604/283 |

Primary Examiner—C. Fred Rosenbaum
Assistant Examiner—Corrine Maglione
Attorney, Agent, or Firm—Nixon & Vanderhye

[57] ABSTRACT

An universal medical connector for manually connecting a first fluid conveying conduit in fluid connection with a patient's vasculature and having a junction terminal with a septum at an end thereof to a second fluid conduit for administration of fluid to a patient. The connector is formed of two elements. The first element defines an integral needle hub, to which a needle is mounted, a base extending from the hub, and fingers extending from the base. The second locking element includes a collar with a support and bars extending therefrom so as to be manually slidable along the first element in the direction the needle extends between a retracted and a locking position in which the connector locks onto a junction terminal and the septum penetrated by the needle. The fingers flex at a flexing line or joint or in a flexure region covered by the bars in the retracted position. Detents are provided on the base and on a detent carrier formed by slots extending into the collar. The bars engage cams on the exterior surface of the fingers to flex the fingers. Inner and outer catches are provided on the interior surface of each finger for respectively engaging larger and smaller junction terminals. The catches are configured so that the disengaging force is substantially independent of septum size.

52 Claims, 6 Drawing Sheets

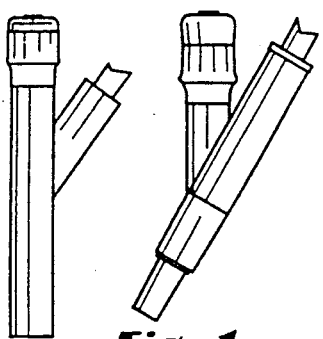
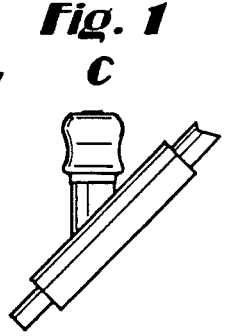
Fig. 1 a
Fig. 1 b
Fig. 1 c
Fig. 1 d
Fig. 1 e
Fig. 1 f
Fig. 3
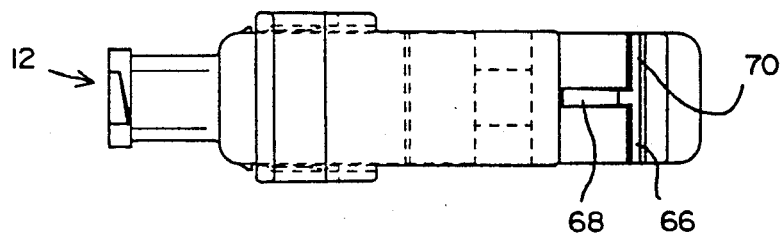
Fig. 4
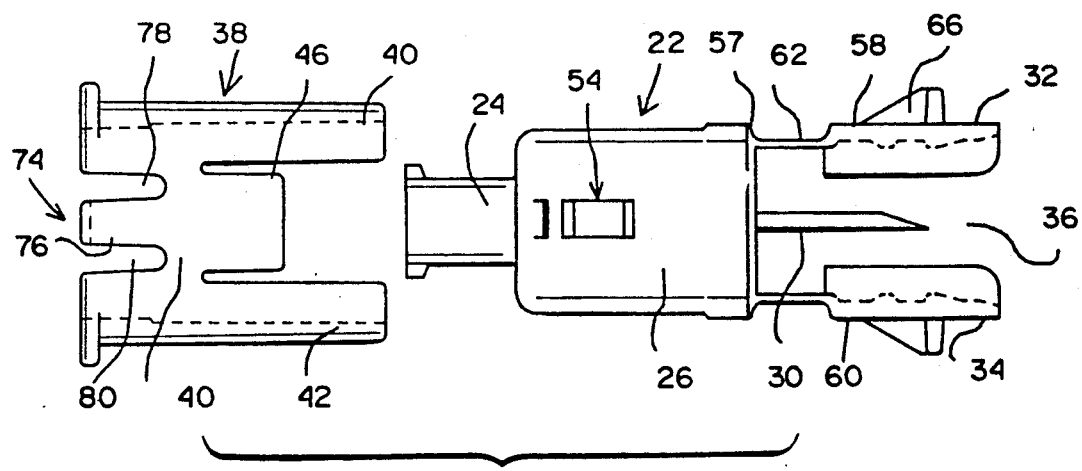

Fig. 15
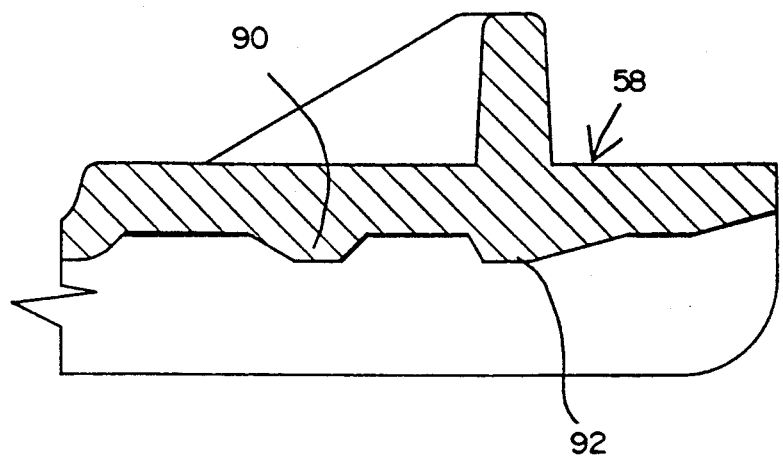
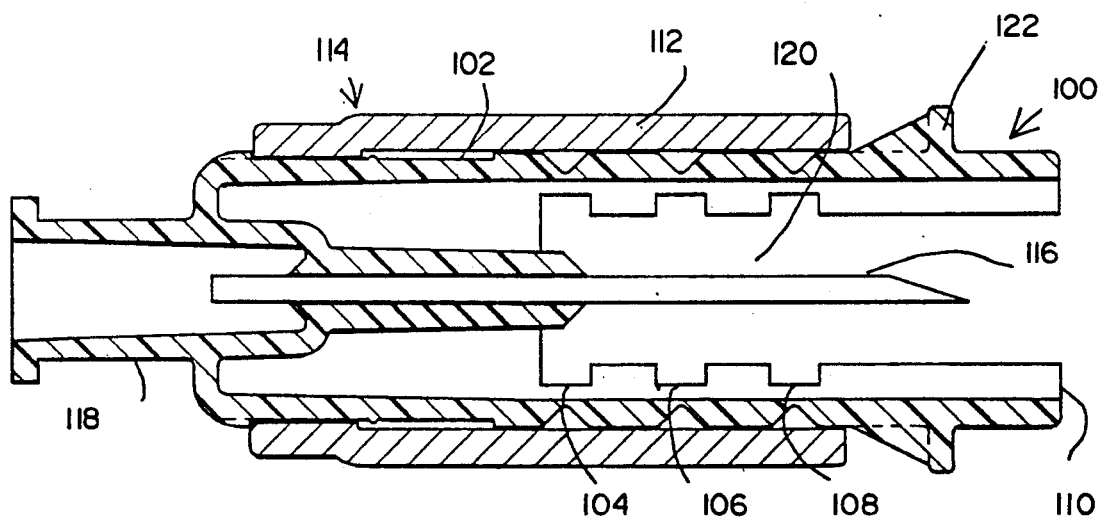
Fig. 16

UNIVERSAL INTRAVENOUS CONNECTOR WITH DUAL CATCHES

This application is a continuation-in-part of application Ser. No. 07/264,533, filed Oct. 31, 1988, now abandoned which in turn is a continuation-in-part of application Ser. No. 07/240,539, filed Sept. 6, 1988, now U.S. Pat. No. 4,946,445, issued Aug. 7, 1990.

BACKGROUND OF THE INVENTION

The invention relates to a universal medical connector for coupling intravenous conduits.

The attachment of intravenous tubing to intravascular catheters for the administration of fluids and medication to patients has been widely utilized for decades. Generally, an intravenous tubing system comprises a segment of tubing which is distally attached to an intravascular catheter inserted into a patient's blood vessel. Such primary conduits usually have junction terminals at an end which are occluded by a penetrable septum. Such a system acts as a primary conduit system. A secondary conduit may be connected to the primary conduit system for the administration of fluids into he patient. The secondary conduit generally has a fluid source a its proximal end and has an open distal end for attachment to the primary conduit system.

FIG. 2a illustrates a conventional primary conduit with its distal end occluded by a septum. In conventional connection, a needle attached to the open end of a secondary conduit is inserted through the septum of the primary conduit to create fluid connection between the fluid source and the catheter.

One major problem with tubing systems is that the needles frequently loosen and become disconnected from the septum during fluid administration. This can result in the medication spilling into the patient's bed or onto the floor. An even greater problem is that the needle may become contaminated through disconnection. Contaminated needle portions may be readvanced through the septum thereby introducing contamination into the primary tubing system.

Yet another problem with existing systems is the danger that the needle poses to heath care workers who must daily make numerous connections and disconnections since the needle may be contaminated by viruses which are present in the blood which can often back up into the primary conduit adjacent the septum. Inadvertent needle stick has long represented one of the greatest problems in the medical field. Not only can needle stick occur during connection and disconnection, but needles occasionally become lost in the bed or elsewhere and provide a continual danger to all workers in the hospital environment. The estimated incidence of needle stick injury is 600,000 to 1,000,000 cases per year and may occur particularly when the nurse is using many very different types of intravenous conduit systems.

Junction terminals and septae come in a wide variety of shapes and sizes. FIG. 1 illustrates the profile of a number of such conventional junction terminals. Commonly, such junction terminals have a head portion which includes a septum which occludes the distal end of the junction terminal. Such junction terminals generally further comprise a rigid tube which extends to the head bearing the septum. The head diameters vary considerably from as little as a 0.301 inches to as much as 0.389 inches, and may be comprised of stretched latex or rigid plastic. Similarly the tube diameters vary from 0.224 inches to 0.330 inches. The head diameter may be virtually the same as the tube diameter or may be substantially greater than the tube diameter. This great variation makes very difficult a universal connector which can reliably and effectively connect and tightly hold or lock onto almost everything that is available in the hospital or medical environment, while at the same time providing substantial protection of health workers and patients from needle contact or stick.

The Ogle Patent No. 4,834,716 demonstrates a shielded needle for insertion into a Y shaped junction terminal. However, the Ogle device provides only a shield and does not provide a secure attachment. Lopez et al., 4,752,292 sows a variety of specifically interfacing devices which include shielded needles intended to provide attachments between primary and secondary tubing systems. However, the disclosed devices have components which must attach to other specific interacting components of a compatible primary system. These devices are not, therefore, compatible with conventional primary systems. Indeed, such devices will not securely attach to the wide range of conventional junction terminals in present use, but rather require the nurse to use a specifically compatible interfacing primary system which may not be readily available. Therefore, none of these devices provides a universal device which can securely lock to the broad range of conventional junction terminals presently in use in medical practice.

SUMMARY OF THE INVENTION

The present invention relates to improvement in a universal medical connector for coupling intravenous conduits as described in a co-pending application of Dr. Lyn filed herewith and entitled "Universal Intravenous Connector with Needle Protection."

The universal connector disclosed ;nd claimed in this copending application is formed of two elements. The first element defines a needle hub adapted to be connected to an open end of a fluid conveying conduit, a needle mounted to the hub, and a base extending from the hub with fingers extending therefrom to define a space through which the needle extends toward an open end, the space being bounded by the fingers.

A second locking element is formed as a collar manually slidable from a retracted position in which a septum can be inserted into the space and penetrated by the needle to locking position flexing the distal position on the fingers to trap and lock onto the septum. The collar has separated bars which extend along the fingers from a support to flex the fingers as the locking element is slid toward the locking position. The needle cannot easily or normally be contacted by the digits of a person using the connector.

According to a first aspect of the present invention, the collar is provided with a detent on a detent carrier which engages a corresponding detent and stop on the outer surface of the base. The Carrier is preferably formed by slots extending inwardly from the end of the collar. The detent carrier acts like a spring, flexing as it is pushed past the corresponding detent. Thus, the collar can be pushed back and forth innumberable times between retracted and locking positions without wearing out the detent or stops.

According to a second aspect of the present invention, each finger is provided with separated catches on its interior surface for engaging the junction terminal and septum. The inner catch primarily engages larger junction terminals and the outer catch engages the conduit for both larger and smaller junction terminals. The catches are configured so that inadvertent disengaging force to separate the two elements is less dependent on junction terminal diameter. The head of the junction terminal therefore releases at a given range of pull forces upon the coupler which is largely independent of junction terminal diameter. This release mechanism prevents an inadvertent forceful pull on the secondary intravenous tube connected to the coupler (such as might occur when the secondary intravenous tube becomes wrapped around a bed rail from damaging the junction terminal.

The release mechanism is provided by the relationship between the pair of catches provided along the interior surface of the distal end of the fingers, and the cam interaction with the bars. More particularly, the inner catch, which engages large junction terminal, gradually slopes in the directions of the open end. Since a junction terminal of larger head diameter will be held by a stronger spring force of the bars, the catch angle is less acute to reduce the holding force against inadvertent displacement. Smaller head diameters result in less spring force end, therefore, a sharper angle is provided with the outer catch to increase the holding force against such displacement.

The sharper angle of the outer catch does not substantially hold the larger diameter terminal because this catch is held away from the head by the more proximal inner catch which abuts the side of the head during displacement. Thus, the connector releases at roughly the same applied force which is less dependent of junction terminal diameter.

Other objects and purposes of the invention will be clear from the following detailed description of the drawings.

BRIEF DESCRIPTION OF THE DRAWINGS

FIGS. 1(a) -1(f) show the profile for a number of typical septae and terminals illustrating the variable configurations.

FIG. 3 shows a side view of the assembled combination.

FIG. 4 shows a top view with the locking element separated from the element defining the needle hub, base, and fingers.

FIG. 15 illustrates a detailed view of the inner and outer catches on each finger.

FIG. 16 shows a further embodiment in which a plurality of flexing regions are provided along the length of each finger.

DETAILED DESCRIPTION OF THE DRAWINGS

Figure 2A:
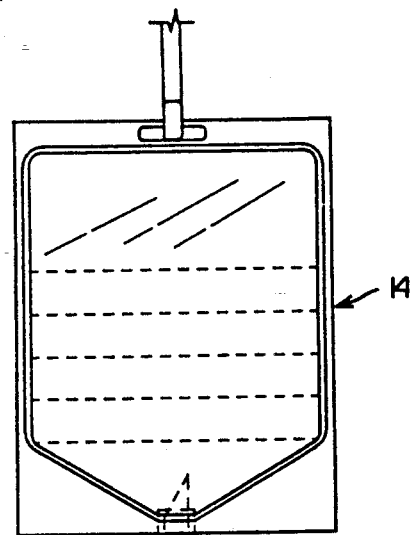
FIG. 2(a) shows a conventional primary conduit, in this case a short heparin well, connected to a catheter within a patient's vein. The primary conduit is shown covered by tape except for the tip bearing the septum.
Figure 2B:
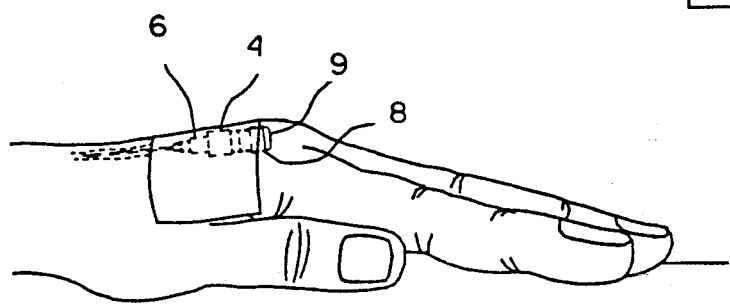
FIG. 2(b) shows the primary conduit of FIG. 2(a) connected to a secondary conduit by the connector of the present invention.
Figure 2B:
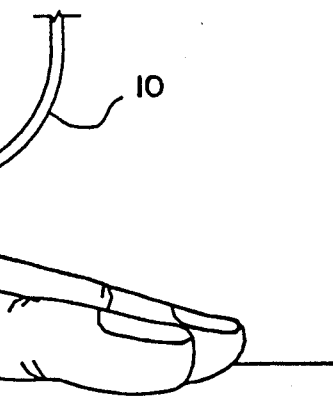

FIG. 2(b) shows a view of the unique connector of the present invention forming part of a system for supplying intravenous fluid to a patient. Primary conduit 4 is shown attached to catheter 6 (shown with its tip in the vein of the dorsun of a patient's hand). Primary conduit 4 has a conventional junction terminal 8 having a septum 9 (the junction terminal 8 is shown partially covered b/ tape as in typical operation.) Secondary conduit 10 is coupled to primary conduit 4 by the universal connector 12 of the present invention, thereby placing bag 14 in fluid communication with the patient's vein.

Reference is now made to FIGS. 3 through 9 which illustrate a preferred embodiment of the present invention. Connector 12 is formed of two distinct elements.

Figure 9:
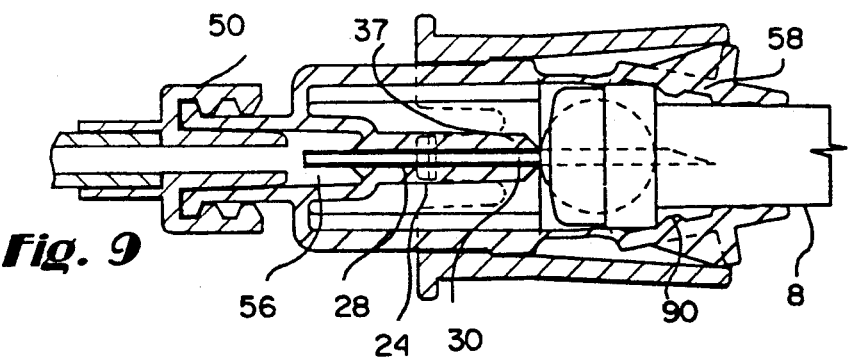
FIG. 9 shows a sectional view of the assembled connector coupling an open ended conduit to a junction terminal and septum having a large head and a large tube.

Element 22 integrally forms a needle hub 24, a base 26 having an inner passage 28 as shown in FIG. 9 through which a cannula, e.g., a needle 30 extends from the proximal hub 24 and a pair of fingers 32 and 34 extending from the base 26 in the direction that the needle 30 extends and bounding an inner space or cavity 36 through which the needle 30 extends. Preferably the base 26 and 24 are integral, but may be formed separately and attached by adhesive or otherwise.

The space or cavity 36 is preferably cylindrical having a length of 0.661 inches and a diameter of 0.436 inches. The proximal end of space 36 is defined by base 26 comprising septum stop 37 as shown in FIG. 9. The length of needle 30 proximal to septum stop 37 is preferably about 0.627 inches. The length of needle 30 from the septum stop to the needle point is about 0.466 inches.

The locking element is integrally formed as a collar 38 having a support portion 40 and further having a pair of arcuate bars 42 and 44 extending therefrom and a pair of shields 46 extending between the bars 42 and 44 from the support portion and separating bars 42 and 44.

Both elements 22 and 28 are formed of a suitable plastic material such as PCTG which is a polyester, a polycarbonate and PCTG blend sold under the trademark EKTR, or an acrylic mutipolymer sod under the trademark CYRO LITE. All these materials are reactively rigid and suitable for use in a medical environment and can be sterilized in accordance with conventional techniques.

Needle hub 24 provides a flange 48 at the proximal end thereof which is readily and conventionally attachable to open ended conduits 50 (FIGS. 9 and 10) of the type now used in hospitals and elsewhere for connection to bottles and bags of fluid and to pumps providing fluid to [e administered into a patient's vein. The distal end 52 of he needle hub 24 remote from the flange 48 is integrally connected to base 26. Base 26 has detent 54 on the exterior surface hereof as can be best seen in FIG. 4. Thus, the lumen through element 22 includes the hub 24 and the cannula, e.g., the needle 30.

Figure 10:
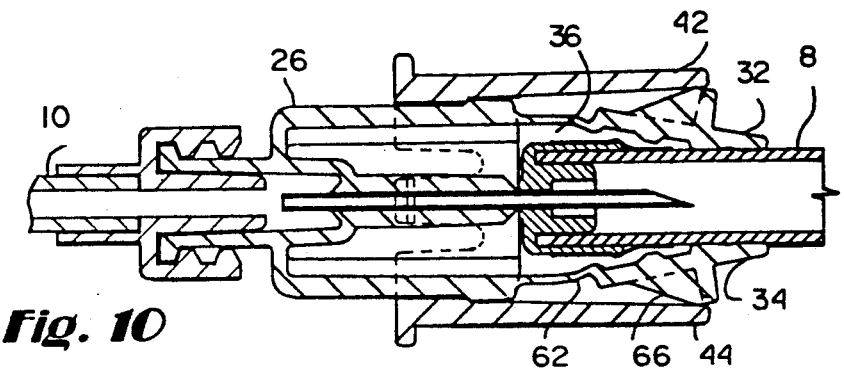
FIG. 10 shows a sectional view on the assembled combination coupled to a junction terminal having a smaller head and tube, and wherein the head diameter is minimally greater than that of the tube.

Needle 30 is conventionally coupled to needle hub 24 and extends through a passage 56 in the needle hub 24 as best seen in FIGS. 9 and 10. A pair of arcuate fingers 32 and 34 integrally extend from the distal end 57 of base 26 (remote from its joinder to needle hub 24) to respective fingertips. Fingers 32 and 34 are formed with distal segments 58 and 60 respectively joined to base 26 by connecting segments defining connecting weakened segments 62 and 64. The connecting segment 62 is preferably between 1 mm and 10 mm in length, preferably less than 5 mm, and preferably greater than 3 mm.

In this embodiment two fingers are provided, but more can be used if desirable or necessary. Preferably the fingers are identical. In operation the fingers flex inwardly with considerably less force than required to make them flex outwardly. Equally important, the fingers spring back to substantially their initial position when the inward force is removed.

Fingers 32 and 34 bound the inner space 36 through which the needle 30 extends and serve to protect users of connector 12 from inadvertent needle stick. On the exterior surface of each of the fingers 32 and 34 is provided a cam portion 66 which is formed as a narrow ramp 68 terminating in a transverse ridge 70 forming with ramp 68 a T-shaped cam portion 66 as can be seen in FIGS. 3 and 4. Ramp 68 is spaced back from &he fingertips of fingers 32 and 34 by a distance which is preferably at least 1 mm and no more than 10 mm. The width of the ramp is preferably about 0.5 mm, but can be 0.4 mm or less or, 0.6 mm or even greater.

A narrow ramp is advantageous in limiting the force which must be applied to overcome friction w[en the locking element 38 is manually shifted from the retracted to the locking positions as will be described hereafter. The ramp height is preferably approximately 3 mm, but may range from 0.5-5 mm or greater depending on the distance the cam is set back from the tips of the fingers. The angle of the ramp is preferably about 30 degrees.

When the collar 38 is assembled with element 22 as illustrated in FIGS. 5-9, detent 54 engages a corresponding hook-like detent 74 on the interior surface of a detent carrier 76, the carrier 76 is formed by slots 78 and 80 extending into support 40. In operation, detent carrier 76 can flex as collar 38 is slid along base 26.

The arcuate bars 42 and 44 each preferably extend no more than 90° about the periphery of the support and base. Alternatively, the bars may be straight posts. The preferable maximum outward flexing of the bars induced by the wedging force of cam 66 is about 0.0885 inches in this embodiment.

In order to lock the connector of the present invention onto a junction terminal 8 having septum 9, the junction terminal 8 is inserted into the space 36 bounded by fingers 32 and 34 so that the needle 30 penetrates septum 9 of terminal 8 and effects fluid communication between the open end 50 of conduit 10 coupled to needle hub 24 and the catheter 6 coupled to the junction terminal 8 of the primary intravenous conduit 4 as shown in FIG. 2(b). When junction terminal 8 is maximally advanced septum 9 will abut septum stop 37 as shown in FIGS. 9–11.

FIGS. 9–13 show the connector of the present invention locked onto various kinds of typical junction terminals. For example as shown, when the collar 38 is manually pushed in the direction of the open end of the space 36 through which needle 30 extends, bars 42 and 44 slide along the fingers 32 and 34 and engage cam portion 66 causing fingers 32 and 34 to flex inwardly. A flexure therefore is defined along the connecting weakened segments 62 and 64 intermediate the base 26 and distal segments 58 and 60. For a large junction terminal 8, such as shown in FIG. 9, the bars 42 and 44 may, in fact, flex slightly outward as the fingers 32 and 34 flex inward. For a smaller junction terminal like that shown in FIG. 10, of course, the flexing of the fingers 32 and 34 will be greater inwardly and the flexing of the bars 42 and 44 outwardly less or non-existent. It is the combination of potential outward flexion of the bars and inward flexion of the fingers which allows the connector to lock onto a wider range of junction tube diameters.

Figure 5:
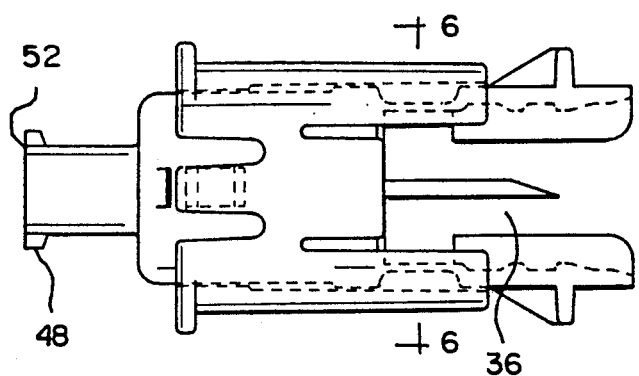
FIG. 5 shows a top view of the assembled combination with the locking collar in the retracted position.
Figure 6:
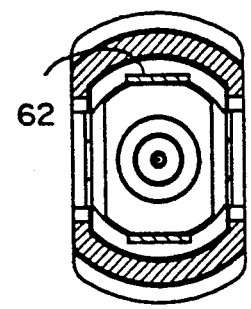
FIG. 6 shows a sectional view of FIG. 5 along the lines 6—6.
Figure 7:
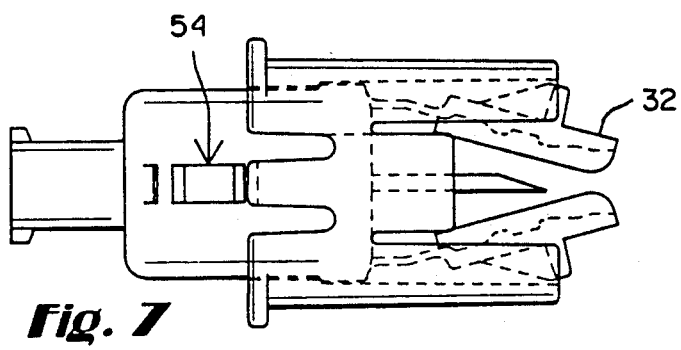
FIG. 7 shows a top view of the assembled connector in the locking position.
Figure 8:
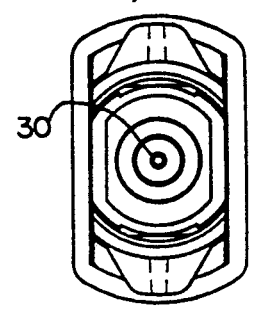
FIG. 8 shows an end view of FIG. 5.

Thus, bars 42 and 44 cooperate with fingers 32 and 34 to define an elastically deformable spring when the collar is moved into the locking position. The spring is deformable, from an original undeformed shape in its retracted position, illustrated, for example, in FIG. 5, by forcible interaction between the junction terminal, the fingers 32 and 34 and the bars 42 and 44 when the junction terminal has been received into the cavity, the collar is moved into its locking position and the fingers are inhibited from flexing inwardly by contacting the junction terminal, as illustrated in FIG. 9. The bars, of course, rebound to their original undeformed shape, as illustrated in FIG. 5, when the collar is returned to its retracted position.

Figure 11:
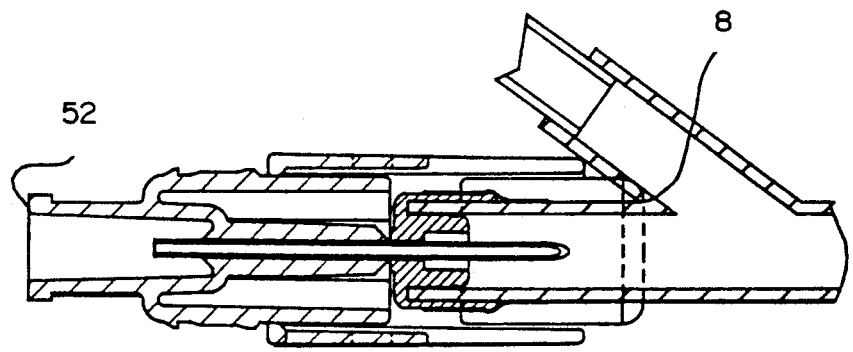
FIG. 11 shows a sectional view of the assembled combination with the locking element in the locking position upon a Y-shaped junction terminal.
Figure 12:
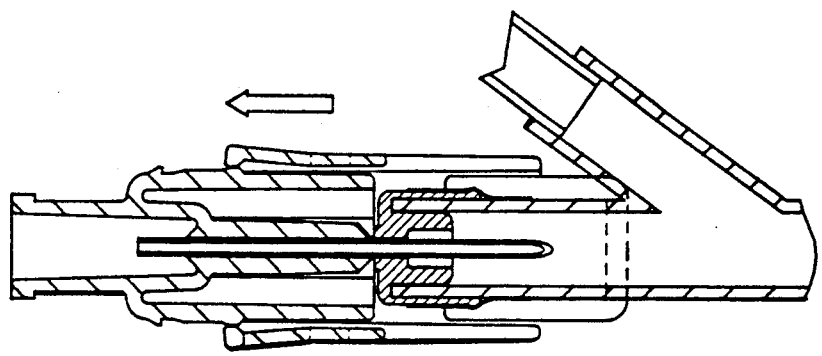
FIG. 12 shows a sectional view of the assembled combination and Y shaped junction terminal of FIG. with the locking element being retracted.
Figure 13:
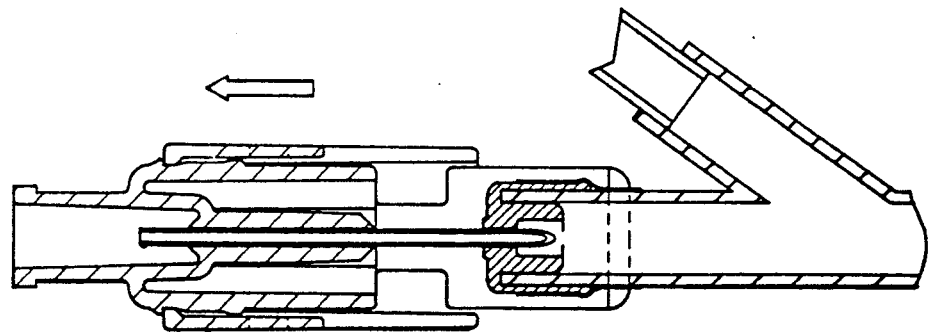
FIG. 13 shows the assembled combination and Y shaped junction terminal of FIGS. 9 and 10 with the locking element fully retracted against the proximal stop.

FIGS. 11 through 13 illustrate how the connector 12 is released as the collar 38 is manually moved between the locking position illustrated in FIG. 11 and the retracted position illustrated in FIG. 13. The junction terminal 8 in this instance is a convention Y-junction.

Figure 14:
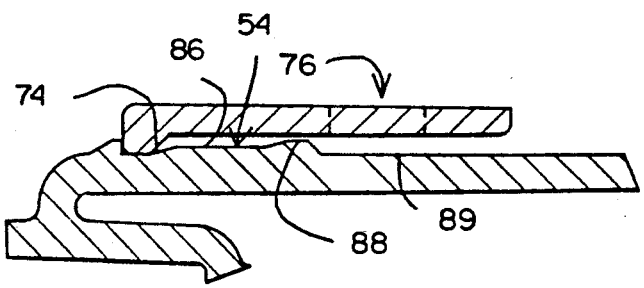
FIG. 14 shows a detailed sectional view illustrating the proximal stop and the detents.

FIG. 14 shows in detail the detent 54 on the base 26 and the corresponding detent 74 on detent carrier 76. The detent 74 on the detent carrier 76 comprises a hook-shaped portion extending downwardly as shown from the end of the detent carrier 76. The detent on the base 26 is formed as a proximal portion 86 with a rising slope which gradually rises to a maximum height at a summit 88 and then abruptly declines in a distal portion 89 back to the original elevation. Making the gradual scope in the direction of movement toward the locking position and the abrupt slope in the opposite direction ensures that minimal force only need be applied to slide collar 38 distally thereby reducing the risk of damage to the vein by pushing too hard on the catheter, while at the same time ensuring that much greater force is required to manually slide the collar 38 in the opposite direction to the retracted position so that inadvertent disconnection is avoided.

Reference is now made to FIG. 15 which illustrates distal segment 58 of one of the fingers 32 and 34 with inner and outer catches 90 and 92. Inner catch 90 is formed with a gradual slope 91 in the direction of the distal end. As shown, for example, in FIG. 9, inner catch 90 engages a large junction terminal 8. When a large junction terminal 8 is engaged as shown in FIG. 9, the bars 42 and 44 are deformed outward to a considerable extent and the spring force is high. Although the spring force is high, the gradual slope 91 of inner catch 90 compensates so that an inadvertent and extremely forceful pull (such as might occur if the secondary tubing inadvertently became wrapped around a bedrail) will allow the connector 12 to disengage from the junction terminal without destroying the junction terminal. Conversely for a small junction terminal, the spring force is less, but the abrupt slope of catch 92 holds the small junction terminal better. The larger junction terminal 8 is not held by the outer catch 92 during a forceful inadvertent pull because inner catch 90 rides over junction terminal 8 swinging outer catch 92 outwardly. Thus, the force necessary to inadvertently disengage without retracting collar 38 is less dependent of junction terminal diameter because the outer catch 92 has a sharper angle than said inner catch 90.

FIG. 16 illustrates an embodiment in which a plurality of weakened regions are provided for gripping a junction terminal by flexing inwardly at different points to provide even greater universality. Each finger 100 extending from base 102 has three weakened regions 104, 106 and 108 between its point of connection to base 102 and its tip 110. As in the other embodiments, regions 104, 106 and 108 are preferably covered by bars 112 extending from collar 114 in the retracted position. Needle 116 extends from hub 118 into space 120 as in the other embodiments. Bars 112 engage cam 122 as described above.

Figure 17A:
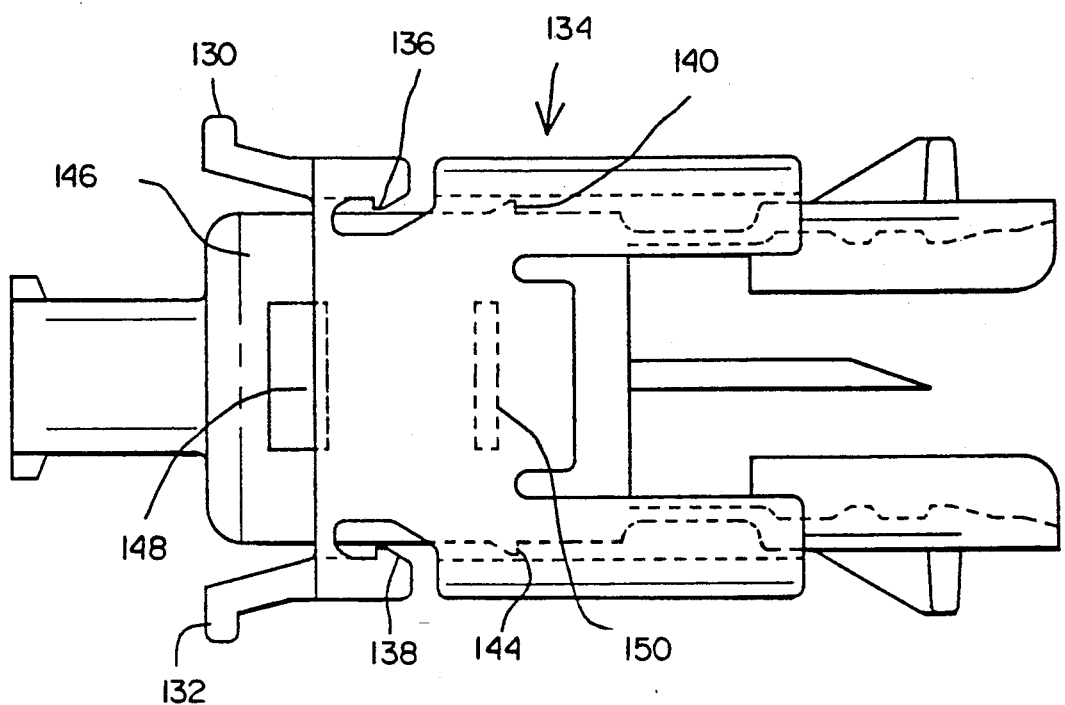
FIGS. 17(a) and (b) show a further embodiment in which the detent carrier flexes outwardly when squeezed.
Figure 17B:
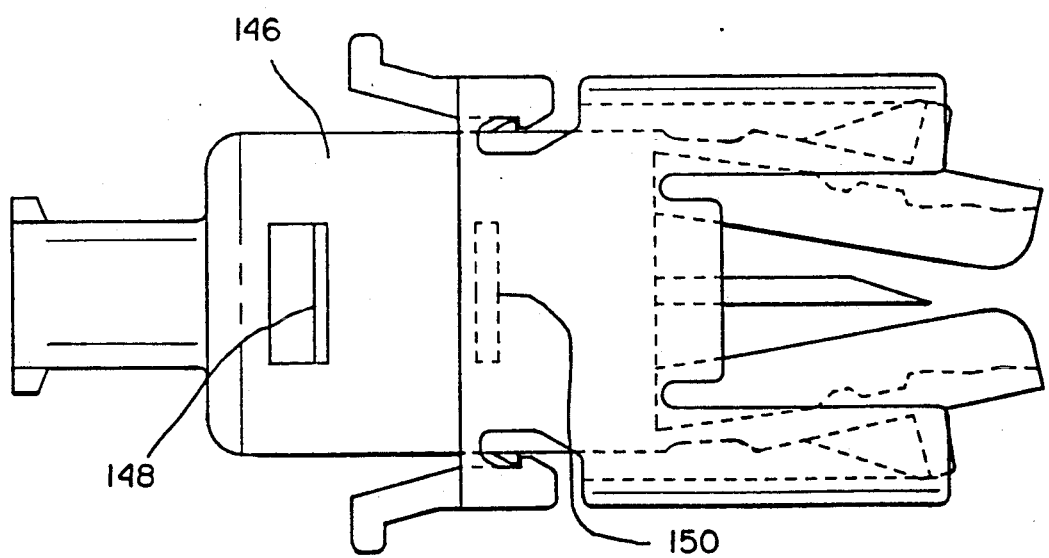

FIGS. 17(a) and 17(b) illustrates a further embodiment in which the force required to slide the collar to the locking position is further minimized. This is achieved by a pair of attached lever arms 130 and 132 which extend outward from collar 134. Arms 130 and 132 respectively have catches 136 and 138 which are pivoted beyond detent 140 and 144 when arms 130 and 132 are manually squeezed. Alternatively, the collar 134 can be slid with catches 136 and 138 riding over the respective detents without squeezing lever arms 130 and 132. However, collar 134 cannot readily be retracted without squeezing so some further security against inadvertent disconnection is provided. In this extended position, collar 134 can be slid without resistance to the locking position shown in FIG. 17(b) engaging detents 142 and 144 of base 146. Stops 148 and 150 are provided on base 146 and function as described above. The other elements and details are as described above.

Many changes and modifications can, of course, be made without departing from the spirit and scope of the invention. For example, the connector could be permanently affixed to an open ended conduit. The connector can be used with junction terminals which have a pre-perforated septum such as a slit for receiving a bunt cannula. Alternatively, the needle may be a blunt cannula which penetrates such pre-perforated septum or slit. Accordingly, the scope of the invention is to be determined by the following claims.

What is claimed is:

1. A universal medical connector for manually connecting and disconnecting a first fluid conveying conduit having a junction terminal with a septum at an end thereof, to a second fluid conveying conduit in fluid connection with a source of fluid for administration to a patient, the second fluid conveying conduit having an open end, comprising:

an element defining an axis and including a base and a lumen extending axially through said base, the lumen having a distal end and a proximal end, said base, adjacent the proximal end of said lumen, being adapted to be coupled to the second fluid conveying conduit adjacent the open end of said conduit;

the base including a cannula projecting axially from said base and fixedly secured to said base, said lumen extending through said cannula for conveying fluid from the second conduit coupled to the end of said base through said cannula;

said base having at least a pair of substantially rigid fingers projecting therefrom in a generally axial direction, said fingers defining a cavity therebetween, the cavity opening in said axial direction through a distal end of said element said cannula extending generally axially from said base toward said distal end of said element, said cannula terminating in a tip short of said distal end of said element, said fingers being movable between (i) a first position adapted for receiving therebetween through said opening and into said cavity the junction terminal of the first fluid conveying conduit so that said cannula may penetrate the septum and fluid may flow through said cannula into the first conduit and (ii) a second position to lock the junction terminal between said fingers and said cavity, said fingers being sized and located in said first and second positions thereof so that said cannula tip is not readily accessible to a human digit; and a collar manually slidable on and toward said distal end of said element between (i) a retracted position enabling said fingers to lie in said first position in which the junction terminal may be received in said cavity through the opening thereof at the distal end of said element and the septum may be penetrated by said cannula and (ii) a position locking said fingers in said second position thereof to trap and lock the junction terminal between said fingers and in said cavity, said collar engaging said fingers in response to sliding movement of said collar on said element toward said locking position to move said fingers inwardly toward said second position thereof;

means disposed along said element adjacent the distal end of said element and cooperable with said fingers for providing a spring when said collar is moved into its locking position, said spring means being elastically deformable from an original substantially undeformed shape in the retracted position of said collar by forcible interaction between the junction terminal, said fingers and said collar when (i) the junction terminal has been received into said cavity, (ii) said collar is moved into its locking position and (iii) said fingers are inhibited from moving inwardly by contacting the junction terminal, said interaction defining a spring force directed generally radially inwardly against the junction terminal, so that junction terminals having a wide range of diameters may be received into said cavity and tightly squeezed between said fingers by said spring force;

said collar being movable from said locking position into said retracted position to release the junction terminal between said fingers, said spring means rebounding to said original shape of said spring means when said collar is returned to its retracted position.

2. A connector according to claim 1 wherein said collar has a proximal portion and a distal portion, and wherein said spring means comprises said distal portion of said collar.

3. A connector according to claim 2 wherein said distal portion of said collar further comprises first and second cantilevered bars projecting in a generally axial direction and toward said distal end of said element, said bars being elastically deformable to flex outwardly upon forcible engagement with said rigid fingers, when said fingers are inhibited from moving inwardly by engagement of said fingers with the junction terminal in said cavity, in response to sliding movement of said collar along said element toward said locking position.

4. A connector according to claim 3 further comprising a ramp on the exterior surface of each rigid finger and engageable by said bars in response to sliding movement of said collar toward said locking position, said engagement operating to move said rigid fingers inwardly toward one another and into said second position to lock the junction terminal between said rigid fingers.

5. A connector according to claim 4 wherein said fingers move inwardly in accordance with the diameter of the junction terminal received in said cavity, said bars being elastically deformable to flex outwardly by forcible engagement with said ramp when said fingers are inhibited from moving inwardly by engagement of said fingers with the junction terminal to said cavity, in response to sliding movement of said collar along said element toward said locking position and movement of said bars against said ramp.

6. A connector assembly to claim 5 wherein at least distal portions of said bars overlie portions of said fingers when said collar lies in said retracted position, said distal portions of said bar and finger portions being arcuate and concentric relative to one another.

7. A connector according to claim 4 wherein said ramp terminates short of the distal end of said finger.

8. A connector according to claim 3 wherein said proximal portion of said collar has a shield portion extending from said proximal portion in a generally axial direction between said bars to at least partially protect said cannula from contamination.

9. A connector according to claim 8 wherein said shield portion is spaced from said bars by a slot on each side of said shield portion thereby affording greater flexibility to said bars.

10. A connector according to claim 2 wherein said distal portion of said collar overlies portions of said rigid fingers when said collar is in said retracted position, said overlying collar portions and said fingers being arcuate and interrupted by flat sides of said collar and said element, respectively, whereby said connector has opposed flat sides affording a low profile and enabling it to lie flat against a surface.

11. A connector according to claim 1 further comprising a flexible and reboundable hinge connecting each said finger with said base.

12. A connector according to claim 11 wherein each said hinge is cantilevered relative to said element and extends axially along said element a predetermined distance so that flexion of said hinge can occur along a variably curved path, each said finger being more rigid than said hinge.

13. A connector according to claim 12 wherein said hinge has a reduced width in comparison with the width of said finger.

14. A connector assembly to claim 12 wherein said hinge is of reduced thickness in comparison with the thickness of said finger.

15. A connector according to claim 12 wherein said hinge comprises a hinge region having a length greater than 2 millimeters.

16. A connector according to claim 12 wherein said hinge region has a length less than 15 millimeters.

17. A connector according to claim 1 wherein said element includes a plurality of hinges separated from each other along the length of said fingers so that junction terminals are grasped by flexing of said fingers inwardly at a plurality of angles.

18. A connector according to claim 1 wherein said cannula comprises a needle.

19. A connector according to claim 1 wherein said base has a detect and said collar has a corresponding detent for engaging said base detent, said detents being configured such that the force required to move the collar from the retracted position to the locking position is less than the force required to move the collar from the locking position to the retracted position.

20. A connector according to claim 1 wherein said rigid fingers have inner and outer catches spaced axially one from the other along interior surfaces of said rigid fingers for trapping and locking respective junction terminals of different sizes.

21. A universal medical connector for manually connecting a first fluid conveying conduit having a junction terminal with a septum at an end thereof, to a second fluid conveying conduit in fluid connection with a source of fluid for administration to a patient, the second fluid conveying conduit having an open end, comprising:

an element defining an axis and including a base and a lumen extending axially through said base, the lumen having a distal end and a proximal end, said base, adjacent the proximal end of said lumen, being adapted to be coupled to the second fluid conveying conduit adjacent the open end of said conduit;

the base including a cannula projecting axially from said base and fixedly secured to said base, said lumen extending through said cannula for conveying fluid from the second conduit coupled to the base through said cannula;

said base having at least a pair of substantially rigid fingers projecting therefrom in a generally axial direction, said fingers defining a cavity therebetween, the cavity opening in said axial direction through a distal end of said element, said cannula extending generally axially from said base toward said distal end of said element, said cannula terminating in a tip short of said distal end of said element, said fingers being movable between (i) a first position adapted for receiving therebetween through said opening and into said cavity the junction terminal of the first fluid conveying conduit so that said cannula may penetrate the septum and fluid may flow through said cannula into the first conduit and (ii) a second position to lock the junction terminal between said fingers and said cavity, said rigid fingers being sized and located in said first and second positions thereof so that said cannula tip is not readily accessible to a human digit; and said element further comprising a hinge connecting said fingers to said base; and a collar manually slidable on and toward said distal end of said element between (i) a retracted position enabling said fingers to lie in said first position in which the junction terminal may be received in said cavity through the opening thereof at the distal end of said element and the septum may be penetrated by said cannula and (ii) a position locking said fingers in said second position thereof to trap and lock the junction terminal between said fingers and in said cavity, said collar engaging said fingers in response to sliding movement of said collar on said element to move said rigid fingers inwardly toward and second position thereof;

said element further comprising a septum stop disposed about said cannula and spaced a fixed distance from the tip of said cannula, said septum stop being remote from the distal end of said cavity and wherein upon advancement of the junction terminal into said cavity, said septum stop is directly contacted by the septum of the junction terminal to limit further advancement of the junction terminal into said cavity, thereby defining a position of maximal advancement of the septum within said cavity, at least a portion of said hinge being positioned along said element distal to said septum stop so that flexion along said hinge can occur distal to said position of maximal advancement of the septum and the septum stop thereby allowing the fingers to flex inwardly at a more acute angle so that junction terminals of widely different diameters can be more tightly locked between said fingers.

22. A universal medical connector for manually connecting a first fluid conveying conduit having a junction terminal with a septum at an end thereof, to a second fluid conveying conduit in fluid connection with a source of fluid for administration to a patient, the second fluid conveying conduit having an open end, comprising:

an element defining an axis and including a base and a lumen extending axially through said base, the lumen having a distal end and a proximal end, said base, adjacent the proximal end of said lumen, being adapted to be coupled to the second fluid conveying conduit adjacent the open end of said conduit;

the base including a cannula projecting axially from said base and fixedly secured to said base, said lumen extending through said cannula for conveying fluid from the second conduit coupled to the proximal end of said lumen through said cannula;

said base having at least a pair of fingers projecting therefrom in a generally axial direction, said fingers having internal wall surfaces defining a cavity therebetween, the cavity having a longitudinal axis and a width defined perpendicular to the longitudinal axis;

said fingers defining an opening extending in said axial direction through a distal end of said element, said cannula extending generally axially from said base toward said distal end of said element, said cannula terminating in a tip short of said distal end of said element, said fingers being flexible between (i) a first position adapted for receiving therebetween through said opening and into said cavity the junction terminal of the first fluid conveying conduit so that said cannula may penetrate the septum and fluid may flow through said cannula into the first conduit and (ii) a second position to lock the junction terminal between said fingers and said cavity, said fingers being sized and located in said first and second positions thereof so that said cannula tip is not readily accessible to a human digit; and a collar manually slidable on and toward said distal end of said element between (i) a retracted position enabling said fingers to lie in said first position in which the junction terminal may be received in said cavity through the opening thereof at the distal end of said element and the septum may be penetrated by said cannula and (ii) a position locking said fingers in said second position thereof to trap and lock the junction terminal between said fingers and in said cavity, said collar engaging said fingers in response to sliding movement of said collar on said element to flex said fingers inwardly toward said second position thereof;

means disposed along each said finger for flexing said fingers, said flexing means being cooperable with each said finger and said collar to forcibly flex each said finger inwardly when said collar is moved from said retracted position toward said locking position;

said internal wall surface of said fingers defining, when said collar is in said locking position, a generally tapering cavity, said cavity tapering in said axial direction toward said distal end of said cavity thereby defining a generally progressive decrease in width of said cavity along said longitudinal axis toward said distal end of said cavity, the taper of said cavity relative to said axis being greater for junction terminal of small diameter and being less for junction terminals of larger diameter, said tapering cavity thereby functioning to accommodate and lock junction terminals of widely different widths within said cavity against said tapering internal wall surfaces.

23. The connector of claim 22 wherein said element further includes a hinge means connecting said fingers to said base, said internal wall surfaces of said fingers extending from said hinge means to said distal end of said cavity, said internal wall surfaces defining, when said collar is in said locking position, a generally tapering cavity, said tapering cavity having a width generally progressively decreasing along said longitudinal axis from adjacent said hinge means toward said distal end of said cavity, said tapering cavity functioning to accommodate and lock junction terminals of widely different widths within said cavity against said altering internal walls.

24. The connector of claim 23 wherein said flexing means comprises a ramp on the exterior surface of each rigid finger and engageable by said collar in response to sliding movement of said collar toward said locking position.

25. The connector of claim 23 further comprising spring means disposed along said element adjacent said distal end of said element when said collar is in said locked position, said spring means being elastically deformable by forcible interaction between the junction terminal, said fingers and said collar when (i) the junction terminal has been received into said cavity, (ii) said collar is moved into its locking position and (ii) said fingers are inhibited from flexing inwardly by contacting the junction terminal, said interaction defining a spring force directed against said junction terminal.

26. A connector according to claim 25 wherein said collar has a proximal portion and a distal portion, and wherein said spring means comprises said distal portion of said collar, said distal portion of said collar further comprising first and second cantilevered bars projecting in said generally axial direction and toward said distal end of said element, said bars being elastically deformable to flex outwardly upon forcible engagement with said fingers, when said fingers are inhibited from flexing inwardly by engagement of said fingers with the junction terminal in said cavity, in response to sliding movement of said collar along said element toward said locking position.

27. A connector according to claim 26 wherein said element further comprises a septum stop disposed about said cannula remote from the distal end of said cavity and wherein upon advancement of the junction terminal into said cavity, said septum stop is directly contacted by the septum of the junction terminal to limit further advancement of the junction terminal into the cavity, thereby defining a position of maximal advancement of the septum within said cavity, at least a portion of said hinge being positioned along said element distal to said septum stop so that flexion along said hinge can occur distal to said position of maximal advancement of the septum thereby allowing the fingers to flex inwardly at a more acute angle so that junction terminals of widely different diameters can be tightly locked between said fingers.

28. A connector according to claim 23 wherein said element further comprises a septum stop disposed about said cannula remote from the distal end of said cavity and wherein upon advancement of said junction terminal into said cavity, said septum stop is directly contacted by the septum of the junction terminal to limit further advancement of the junction terminal into the cavity, thereby defining a position of maximal advancement of the septum within said cavity, at least a portion of said hinge being positioned along said element distal to said septum stop so that said flexion along said hinge can occur distal to said position of maximal advancement of the septum thereby allowing the fingers to swing inwardly at a more acute angle so that junction terminals of widely different diameters can be tightly locked between said fingers.

29. A connector according to claim 28 wherein said hinge is cantilevered and extends axially along a predetermined distance so that flexion of said hinge can occur along a variably curved path, said finger being more rigid than said hinge.

30. A connector according to claim 22 wherein said fingers have inner and outer catches spaced axially one from the other along interior surfaces of said fingers for trapping and locking respective junction terminals of different sizes.

31. A universal medical connector for manually connecting a first fluid conveying conduit having a junction terminal with a septum at an end thereof, to a second fluid conveying conduit in fluid connection with a source of fluid for administration to a patient, the second fluid conveying conduit having an open end, comprising:

an element defining an axis and including a base and a lumen extending axially through said base, the lumen having a distal end and a proximal end, said base, adjacent the proximal end of said lumen, being adapted to be coupled to the second fluid conveying conduit adjacent the open end of said conduit;

the base including a cannula projecting axially from said base and fixedly secured to said base, said lumen extending through said cannula for conveying fluid from the second conduit coupled to the base through said cannula;

said base having at least a pair of substantially rigid fingers projecting therefrom in a generally axial direction and being circumferential spaced one from the other about the axis of said element, said fingers defining a cavity therebetween, the cavity opening in said axial direction through a distal end of said element, said cannula extending generally axially from said base toward said distal end of said element, said cannula terminating a a tip short of said distal end of said element, said fingers being movable between (i) a first position adapted for receiving therebetween through said opening and into said cavity the junction terminal of the first fluid conveying conduit so that said cannula may penetrate the septum and fluid may flow through said cannula into the first conduit and (ii) a second position to lock the junction terminal between said fingers and said cavity, said rigid fingers being sized and located in said first and second positions thereof to that said cannula tip is not readily accessible to a human digit; and a collar manually slidable on and toward said distal end of said element between (i) a retraced position enabling said fingers to lie in said first position in which the junction terminal may be received in said cavity through the opening thereof at the distal end of said element and the septum may be penetrated by said cannula and (ii) a position locking said fingers in said second position thereto to trap and lock the junction terminal between said fingers and in said cavity, said collar engaging said fingers in response to sliding movement of said collar on said element to move said rigid fingers inwardly toward said second position thereof;

said collar further comprising first and second discrete cantilevered spring portions circumferentially spaced one from the other about said axis and projecting from said collar toward said distal end of said element, said cantilevered portions being deformable to flex outwardly by said rigid fingers, when said fingers are inhibited from moving inwardly by engagement thereof with the junction terminal in said cavity, in response to sliding movement of said collar along said element toward said locking position, to define a laterally inwardly directed spring force thereby enabling junction terminals of different diameters to be tightly squeezed between said fingers by said spring force in the locked position of said collar.

32. A connector according to claim 31 including a ramp on the exterior surface of each rigid finger and engageable by said collar in response to sliding movement of said collar toward said locking position, said engagement operating to move said rigid fingers inwardly toward one another and into said second position to lock the junction terminal between said rigid fingers.

33. A connector according to claim 32 said cantilevered collar portions are flexible outwardly by a distance at least equal to 25% of the height of said ramps, when said fingers are inhibited from moving inwardly by engagement thereof with the junction terminal in said cavity, in response to further sliding movement of said collar along said element toward said locking position.

34. A connector according to claim 31 wherein said collar has a distal portion, said distal portion of said collar engaging said fingers when the collar is in the retracted position such that a greater force is required to cause outward movement of said rigid fingers than is required to cause inward movement of said rigid fingers when the collar lies in its retracted position to substantially preclude outward movement of the fingers so as to prevent a human digit from moving the fingers outwardly and contacting the tip of said cannula.

35. A connector according to claim 31 wherein the base is provided with at least one stop which engages said collar for preventing further sliding of said collar when said collar reaches said locking position.

36. A connector according to claim 31 wherein said collar further comprises a support portion and said cantilevered collar portions further comprise respective first and second bars extending from one end of said support portion to in part overlie said rigid fingers in said retracted position of said collar to substantially preclude outward movement of said rigid fingers so as to prevent a human digit from moving the fingers outwardly and contacting the tip of said cannula, said support portion having a shield portion extending from said one end of said support portion between said bars to protect said cannula from contamination.

37. A connector according to claim 36 wherein said shield portion is spaced from said bars by a slot on each side of said shield portion thereby affording greater flexibility to said bars.

38. A connector according to claim 31 wherein said base has a detent and said collar has a corresponding detent from engaging said base detent, said detents being configured such that the force required to move the collar from the retracted position to the locking position is less than the force required to move the collar from the locking position to the retracted position.

39. A connector according to claim 38 including means cooperable between said collar and said element to gradually increase the force required to move the collar as said collar is advanced toward said locking position, said force gradually increasing as said collar is advanced along a distance of greater than 0.5 millimeters.

40. A connector according to claim 31 wherein said element has a septum stop for engagement by the septum of the junction terminal upon maximum advancement of the junction terminal into said cavity and penetration of the septum by said cannula, said element further comprising a hinge proximal to each said rigid finger and positioned along said element so that at least a portion of said hinge is distal to said septum stop.

41. A connector according to claim 31 wherein said element has a hinge proximal to each said rigid finger further enabling movement of said rigid finger by flexion at said hinge, each said hinge comprising a connecting spring segment intermediate the rigid finger and the base and wherein said segment has greater flexibility than said rigid finger.

42. A connector according to claim 31 wherein said element has a hinge proximal to each said rigid finger enabling movement of said rigid finger by flexion at said hinge, said hinge extending axially along said finger a predetermined distance and being of reduced dimension in a direction transverse to the axial direction in comparison with a corresponding dimension in the same direction of said rigid finger so that flexion of said hinge region can occur along a variably curved path.

43. A connector according to claim 31 wherein said cannula comprises a needle, said element further comprising a hinge proximal to each said rigid finger enabling movement of said rigid finger by flexion at said hinge, said hinge further comprising a hinge region having an axial length greater than 1 millimeter and less than 15 millimeters.

44. A connector according to claim 31 wherein the element has a hinge proximal to each said rigid finger enabling movement of said rigid finger by flexion at said hinge, each said hinge comprising a connecting spring segment intermediate the rigid finger and the base and wherein said segment has greater flexibility than said rigid finger, said cantilevered collar portions further comprising respective first and second bars in part overlying said rigid fingers in said retracted position of said collar to substantially preclude outward movement of said rigid fingers, and a ramp cooperable between said fingers and said bars and responsive to sliding movement of said collar toward said locking position to flex said fingers inwardly toward one another in accordance with the size of the junction terminal received in said cavity and into said second position to lock the junction terminal between said fingers, said bars being flexible outwardly, when said fingers are inhibited from flexing inwardly by engagement thereof with the junction terminal in said cavity, in response to further sliding movement of said collar along said element toward said locking position.

45. A connector according to claim 44 wherein said collar includes a support portion and a shield portion extending from said support portion toward said distal end of said element, said shield portion being spaced from said bars by a slot on each side of said shield portion thereby affording flexibility to said bars, said bars and said rigid fingers being arcuate, said bars having distal ends thereof overlying at least portion of said fingers in the retracted position of said collar, said distal ends of said bars and said fingers portions being concentric one with the other.

46. A connector according to claim 31 wherein said base has a detent along an exterior surface thereof, said collar having a detent carrier formed by slots extending inwardly from the end of said collar remote from the distal end of said element, and a detent on said carrier for engaging the detent on said base, said detents being configured such that the force required to move the collar from the retracted position to the locking position is less than the force required to move the collar from the locking position to the retracted position.

47. A connector according to claim 46 wherein the force required to move the collar gradually increases as said collar is advanced toward said locking position.

48. A connector according to claim 31 wherein said rigid fingers have inner and outer catches spaced axially one from the other along the interior surfaces of said rigid fingers for trapping and locking respective junction terminals of different sizes.

49. A connector according to claim 31 wherein said base has a catch provided on the exterior surface thereof, said collar having a lever pivotally attached thereto and having a catch engageable with said catch on said base, said lever being pivotable by applied manual force so that said collar can slide along said base.

50. A universal medical connector for manually connecting a first fluid conveying conduit having a junction terminal with a septum at an end thereof, to a second fluid conveying conduit in fluid connection with a source of fluid for administration to a patient, the second fluid conveying conduit having an open end, comprising:

an element defining an axis and including a base and a lumen extending axially through said base, the lumen having a distal end and a proximal end, said base, adjacent the proximal end of said lumen, being adapted to be coupled to the second fluid conveying conduit adjacent the open end of said conduit;

the base including a cannula projecting axially from said base, said lumen extending through said cannula for conveying fluid from the second conduit coupled to the proximal end of said lumen through said cannula;

said base having at least a pair of substantially rigid fingers projecting therefrom in a generally axial direction and being circumferentially spaced one from the other about the axis of said element, said fingers defining a cavity therebetween, the cavity opening in said axial direction through a distal end of said element, said cannula extending generally axially from said base toward said distal end of said element, said cannula terminating in a tip short of said distal end of said element, said fingers being movable between (i) a first position adapted for receiving therebetween through said opening and into said cavity the junction terminal of the first fluid conveying conduit so that said cannula may penetrate the septum and fluid may flow through said cannula into the first conduit and (ii) a second position to lock the junction terminal between said fingers and said cavity, said rigid fingers being sized and located in said first and second positions thereof so that said cannula tip is not readily accessible to a human digit; and a collar manually slidable on and toward said distal end of said element between (i) a retracted position enabling said fingers to lie in said first position in which the junction terminal may be received in said cavity through the opening thereof at the distal end of said element and the septum may be penetrated by said cannula and (ii) a position locking said fingers in said second position thereto trap and lock the junction terminal between said fingers and in said cavity, said collar engaging said fingers in response to sliding movement of said collar on said element to move said rigid fingers inwardly toward said second position thereof;

said collar further comprising first and second cantilevered portions circumferentially spaced one from the other about said axis and projecting from said collar toward said distal end of said element, said cantilevered portions being deformable to flex outwardly by said rigid fingers, when said fingers are inhibited from moving inwardly by engagement thereof with the junction terminal in said cavity, in response to sliding movement of said collar along said element toward said locking position;

said collar further comprising a support portion and said cantilevered collar portions further comprising respective first and second bars extending from one end of said support portion to in part overlie said rigid fingers in said retracted position of said collar to substantially preclude outward movement of said rigid fingers so as to prevent a human digit from moving the fingers outwardly and contacting the tip of said cannula, the overlying parts of said bar and said rigid fingers being arcuate with each rigid finger and its overlying bar part being concentric.

51. A universal medical connector for manually connecting a first fluid conveying conduit having a junction terminal with a septum at an end thereof, to a second fluid conveying conduit in fluid connection with a source of fluid for administration to a patient, the second fluid conveying conduit having an open end, comprising:

an element defining an axial and including a base and a lumen extending axially through said base, the lumen having a distal end and a proximal end, said base, adjacent the proximal end of said lumen, being adapted to be coupled to the second fluid conveying conduit adjacent the open end of said conduit;

the base including a cannula projecting axially from said base, said lumen extending through said cannula for conveying fluid from the second conduit coupled to the proximal end of said lumen through said cannula;

said base having at least a pair of substantially rigid fingers projecting therefrom in a generally axial direction and being circumferentially spaced one from the other about the axis of said element, said fingers defining a cavity therebetween, the cavity opening in said axial direction through a distal end of said element, said cannula extending generally axially from said base toward said distal end of said element, said cannula terminating in a tip short of said distal end of said element, said fingers being movable between (i) a first position adapted for receiving therebetween through said opening and into said cavity the junction terminal of the first fluid conveying conduit so that said cannula may penetrate the septum and fluid may flow through said cannula into the first conduit and (ii) a second position to lock the junction terminal between said fingers and said cavity, said rigid fingers being sized and located in said first and second positions thereof so that said cannula tip is not readily accessible to a human digit; and a collar manually slidable on and toward said distal end of said element between (i) a retracted position enabling said fingers to lie in said first position in which the junction terminal may be received in said cavity through the opening thereof at the distal end of said element and the septum may be penetrated by said cannula and (ii) a position locking said fingers in said second position thereof to trap and lock the junction terminal between said fingers and in said cavity, said collar engaging said fingers in response to sliding movement of said collar on said element to move said rigid fingers inwardly toward said second position thereof;

said collar further comprising first and second cantilevered portions circumferentially spaced one from the other about said axis and projecting from said collar toward said distal end of said element, said cantilevered portions being deformable to flex outwardly by said rigid fingers, when said fingers are inhibited from moving inwardly by engagement thereof with the junction terminal in said cavity, in response to sliding movement of said collar along said element toward said locking position;

said first and second cantilevered portions of said collar in part overlying respective portions of said rigid fingers in said first position thereof and in the retracted position of said collar to substantially preclude outward movement of said rigid fingers so as to prevent a human digit from moving the fingers outwardly and contacting the tip of the cannula, said cantilevered collar portions and said rigid fingers being arcuate and interrupted by flat sides of said collar and said element, respectively, whereby said connector has opposed flat sides affording a low profile and enabling it to lie flat against a surface.

52. In an intravenous fluid administration system for administration of fluid into a patient vein, the system having a first fluid conveying conduit for fluid connection with a patient's vein and having a junction terminal with a septum at an end thereof, a receptacle for containing intravenous fluid, and an elongated flexible second fluid conveying conduit having a distal end, said second conduit being in fluid connection proximally with said receptacle and wherein the improvement comprises, in combination:

a medical connector in fluid connection with said second conduit at the distal end of said second conduit;

said medical connector including an element defining an axis and including a base and a lumen extending axially through said base, the lumen having a distal end and a proximal end said base, adjacent the proximal end of said lumen, adapted to be coupled to the second fluid conveying conduit adjacent the distal end of said second conduit;

the base including a cannula projecting axially from said base, said lumen extending through said cannula for conveying fluid from the second conduit coupled to the proximal end of said lumen through said cannula;

said base having a pair of oppositely opposed rigid fingers projecting therefrom in a generally axial direction and being circumferentially spaced one from the other about the axis of said element, said fingers defining a cavity therebetween, the cavity opening in said axial direction through a distal end of said element, said cannula extending generally axially from said base toward said distal end of said element, said cannula terminating in a tip short of said distal end of said element, said fingers being movable between (i) a first position adapted for receiving therebetween through said opening and into said cavity the junction terminal of the first fluid conveying conduit so that said cannula may penetrate the septum and fluid may flow through said cannula into the first conduit and (ii) a second position to lock the junction terminal between said fingers and said cavity, said rigid fingers being sized and located in said first and second positions thereof so that said cannula tip is not readily accessible to a human digit; and a collar manually slidable on and toward said distal end of said element between (i) a retracted position enabling said fingers to lie in said first position in which the junction terminal may be received in said cavity through the opening thereof at the vital end of said element and the septum may be penetrated by said cannula and (ii) a position locking said fingers in said second position thereof to trap and lock the junction terminal between said fingers and in said cavity, said collar engaging said fingers in response to sliding movement of said collar on said element to move said rigid fingers inwardly toward said second position thereof;

said collar further comprising first and second separate and discrete oppositely disposed cantilevered bars circumferentially spaced one from the other about said axis and projecting from said collar toward said distal end of said element, said cantilevered bars overlying said fingers in said locking position of said collar.

* * * * *